United States Patent [19]
Klein et al.

[11] Patent Number: 6,075,029
[45] Date of Patent: Jun. 13, 2000

[54] XANTHINE MODULATORS OF METABOLISM OF CELLULAR P-450

[75] Inventors: J. Peter Klein, Vashon; Anil M. Kumar, Seattle; Paul Woodson, Edmonds, all of Wash.

[73] Assignee: Cell Therapeutics, Inc., Seattle, Wash.

[21] Appl. No.: 09/002,345

[22] Filed: Jan. 2, 1998

[51] Int. Cl.⁷ ........................ A61K 31/52; C07D 473/10; C07D 473/06
[52] U.S. Cl. .......................... 514/264; 514/265; 544/229; 544/267; 544/268; 544/269; 544/270; 544/271
[58] Field of Search ..................................... 514/263, 264, 514/265; 544/268, 269, 270, 271, 267, 229

[56] References Cited

U.S. PATENT DOCUMENTS

| | | | |
|---|---|---|---|
| 3,422,307 | 1/1969 | Langer et al. | 315/150 |
| 3,737,433 | 6/1973 | Mohler et al. | 260/256 |
| 4,576,947 | 3/1986 | Hinze et al. | 514/263 |
| 4,636,507 | 1/1987 | Kreutzer et al. | 514/263 |
| 4,833,146 | 5/1989 | Gebert et al. | 514/263 |
| 4,965,271 | 10/1990 | Mandell et al. | 514/263 |
| 5,039,666 | 8/1991 | Novick, Jr. | 514/39 |
| 5,096,906 | 3/1992 | Mandell et al. | 514/263 |
| 5,338,741 | 8/1994 | Fumeaux | 514/262 |
| 5,470,579 | 11/1995 | Bonte | 514/263 |
| 5,629,423 | 5/1997 | Klein et al. | 544/48 |

OTHER PUBLICATIONS

Goodman et al., The Pharmacological Basis of Therapeutics, *Macmillan Publishing Company*, (1985), pp. 5 and 15.

Segura et al., Journal of Pharmacy and Pharmacology, *J. Pharceutical Pharmacology*, The Pharmaceutical Society of Great Britain, (Mar. 1986), pp. 615–618.

Tarrus et al., British Journal of Clinical Pharmacology, *The British Pharmacological Society By Blackwell Scientific Publications Ltd.*, Inhibition of Caffeine Metabolism, (1987), vol. 23, pp. 9–18.

Lillibridge et al., Drug Metabolism and Disposition: Biological Fate of Chemicals, *American Society for Pharmacology and Experimental Therapeutics*, (1973), vol. 24, No. 11 pp. 1174–1179.

Peter F. Guengerich, Mammalian Cytochromes P–450, *CRC Press, Inc.* vol. II, pp. 1–17, (1987).

*Primary Examiner*—Mark L. Berch
*Attorney, Agent, or Firm*—Foley & Lardner

[57] ABSTRACT

A new class of xanthine compounds, variously substituted at the 1, 3, 7 and 8 positions, is characterized by an ability to modulate the activity of key enzymes involved in drug metabolism. These compounds generally are useful in affecting drug metabolism and, particularly, in extending the circulating half-life of compounds that are metabolized via P-450-mediated pathways.

14 Claims, No Drawings

XANTHINE MODULATORS OF METABOLISM OF CELLULAR P-450

FIELD OF THE INVENTION

The present invention relates to a new class of xanthine compounds, variously substituted at the 1, 3, 7 and 8 positions, which possess the ability to modulate the activity of key enzymes involved in drug metabolism. More specifically, the invention relates to 3,8- and 3,7,8-substituted xanthines which also are substituted at the 1-position with a straight-chain hydroxyalkyl group. The inventive compounds are useful as antagonists of cellular P-450 in the context, for example, of extending the circulating half-life of pharmaceutical agents that are metabolized through P-450-mediated pathways.

BACKGROUND OF THE INVENTION

For many drugs, a key hurdle to effective oral delivery is the "first pass" effect. See GOODMAN AND GILMANS: THE PHARMACOLOGICAL BASIS OF THERAPEUTICS, pages 5 and 15 (Macmillan Publishing Co. 1985) ("Goodman and Gilman's"). Upon oral administration, a pharmaceutical agent is taken up by the lumen of the stomach and enters the portal vein. The portal vein delivers this agent to the liver before it is passed to the rest of the body. On this first pass, high levels of catabolic enzymes in the liver results in significant metabolism of the drug before it can reach its intended site of action, thereby increasing the amount of drug required for efficacious treatment.

Methylxanthines define a category of pharmaceutical agents substantially affected by the first pass effect. Illustrative of the methylxanthines are caffeine, theophylline, theobromine, aminofylline, pentoxifylline, and lisofylline, (R)-1-(5-hydroxyhexyl)-3,5-dimethylxanthine (LSF). Methylxanthines are important therapeutic compounds, useful in treating a wide variety of clinical indications. See Goodman and Gilman's at pages 589–603, for example, as well as U.S. Pat. No. 3,422,307, U.S. Pat. No. 3,737,433, U.S. Pat. No. 4,515,795, U.S. Pat. No. 4,576,947, U.S. Pat. No. 4,636,507, U.S. Pat. No. 4,833,146, U.S. Pat. No. 4,965,271, U.S. Pat. No. 5,039,666, and U.S. Pat. No. 5,096,906.

Although Methylxanthines are absorbed quickly and efficiently via oral, rectal and parenteral routes, they are significantly metabolized by liver enzymes. This metabolism results in decreased circulating drug levels and, hence, decreasing bioavailability. In practical terms, therefore, larger quantities of drug must be administered to the patient, raising cost concerns and the possibility of accumulating toxic metabolites.

The cytochrome P-450 superfamily of isozymes serves a predominant role in hepatic drug metabolism. They have been implicated in the metabolism of a significant number of divergent bioactive compounds, including methylxanthines. Yang et al., "The diversity of substrates for cytochrome P-450" in II MAMMALIAN CYTOCHROME P-450 2–17 (CRC Press 1987). Given the number and highly variable specificities of the P-450 isozymes, however, it is nearly impossible to predict which isoform is responsible for the metabolism of a particular compound. Even if the particular responsible isozyme were known, moreover, no methods currently exist for rationally designing effective inhibitors of enzymes with such substrate specificity.

Accordingly, an unmet need exists for compounds and methods that inhibit the metabolism of target pharmaceutical agents during treatment. In particular, there is a substantial need for compounds and methods that can be used to modulate cellular P-450 metabolism and, thereby influence, and specifically increase, circulating levels of such pharmaceuticals. The need is especially acute for compounds and methods that provide for higher circulating levels of methylxanthines.

SUMMARY OF THE INVENTION

It is therefore an object of the present invention to provide compounds useful for modulating circulating levels of pharmaceutical agents.

It is a further object of the invention to provide a therapeutic approach to modulating circulating levels of a drug.

In accomplishing these and other objectives, the present invention provides novel substituted xanthine compounds which inhibit cellular P-450, and pharmaceutical compositions containing such compounds. Also provided are methods that utilize the inventive xanthine compounds to treat a patient, particularly in the context of increasing circulating half-life of a therapeutic agent that is metabolized by cellular P-450. The therapeutic agent thus affected can be an inventive xanthine compound itself or other compounds that are metabolized by P-450.

DETAILED DESCRIPTION OF PREFERRED EMBODIMENTS

Introduction

By virtue of the first pass effect, agents that inhibit liver-mediated drug metabolism would be expected to increase circulating levels of these target pharmaceutical agents. In fact, agents that alter the levels of drug metabolizing enzymes in the liver directly influence circulating serum levels of methylxanthines. Thus, agents that increase liver metabolism tend to decrease methylxanthine serum levels; conversely, agents that decrease liver metabolism tend to decrease these levels. By the same token, the inventive compounds can be used to inhibit hepatic metabolism of a target pharmaceutical agent, such as a methylxanthine, and thereby provide increased serum levels of the medicament.

Caffeine (1,3,7-trimethylxanthine) is exemplary of a methylxanthine for which there is some understanding as to metabolism. The search for a replacement for the asthma drug theophylline (1,3-dimethylxanthine) lead to the development of the related substituted methylxanthine compound furafylline, 1,8-dimethyl-3-(2'furfuryl)-methylxanthine (FRF). Segura et al., *J. Pharm. Pharmacol.* 38: 615–18 (1986). During clinical trials with furafylline, elevated serum caffeine levels were observed in patients treated with the drug. Tarrus et al., *Br. J. Clin. Pharmacol.* 23: 9–18 (1987). It subsequently was shown that furafylline causes this accumulation by inhibiting the P-450 isozyme, P-450IA2, which catalyzes N3 demethylation of caffeine in the liver. Sesardic et al., *Br. J. Pharmacol.* 29: 651–63 (1990). Thus, furafylline inhibits caffeine metabolism, by inhibiting N3 demethylation, and increases the circulating half-life of caffeine.

Furafylline was observed to increase the circulating half-life of the methylxanthine compound LSF when co-administered with that drug. The present inventors hypothesized that this result derived from furafylline-mediated inhibition of LSF metabolism. In other words, this result was understood to implicate P-450IA2 as at least one enzyme involved in the normal clearance of LSF. Because of the large number of P-450 enzymes with broad, overlapping specificities, however, it was thought unlikely that this isozyme was exclusively or even predominantly responsible for the metabolism of LSF and related methylxanthine compounds.

Indeed, whereas P-450IA2 mediates demethylation of caffeine at the N3 position of the xanthine ring, this does not seem to be the case with LSF metabolism or with metabolism of the related methylxanthine pentoxifylline (PTX). Lillibridge et al., Drug Metabolism Disposition 24:1174–79 (1996). The primary metabolites of LSF and PTX result from modification of the N1 substituent, not the N3 substituent. This strongly indicates that PTX and LSF are inactivated in a manner different from caffeine. Indeed, inactivation of these drugs does not appear to involve a dealkylation at all.

Thus, metabolic inhibitors for one or more P-450 pathways responsible for in vivo inactivation of methylxanthine compounds, and particularly inhibitors for pathways that inactivate LSF and related methylxanthines, are desired for increasing the available levels of methylxanthines. The inventive compounds and methods resulted from efforts to obtain alternative and effective inhibitors of such pathways.

Compounds of the Invention

The compounds of the invention are substituted xanthine compounds having an ability to inhibit cellular P-450. Preferred compounds within this category have the following formula:

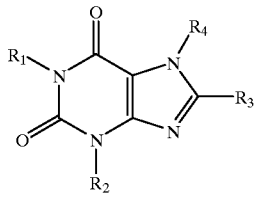

where the $R_1$ substituent is independently a resolved enantiomer or a racemic mixture of an ω-1 secondary alcohol-substituted C5–C8 alkyl, optionally containing one or two nonadjacent oxygen atoms in place of a carbon atom. Some preferred compounds have $R_1$ as a C6 alkyl with the hydroxyl group as the R or S enantiomer. Other preferred compounds have $R_1$ as a C6 alkyl with the hydroxyl group as the R enantiomer.

The $R_2$ substituent is a C1–C20 alkyl or a C2–C20 alkenyl or alkynyl, which optionally contains one or two nonadjacent N or O atoms in place of a carbon atom in the chain. $R_2$ preferably is substituted by at least one member of the group $R_5$. In some preferred compounds the chain of $R_2$ is 1 to 7 atoms long and in others it is simply a methyl group, in any case it is preferably substituted by at least one member of the group $R_5$.

The $R_3$ substituent is a substituted or unsubstituted, straight or branched chain moiety of the formula —$CH_2$—Y. Y is a C1–C7 alkyl, C2–C7 alkenyl, or C2–C7 alkynyl. Some preferred compounds have $R_3$ as a straight or branched chain C1–C6 alkyl. Other preferred compounds have $R_3$ as a methyl group.

The $R_4$ substituent is hydrogen or a moiety having the formula —$CH_2$—Y, as defined for $R^3$. In certain preferred compounds, $R^4$ is a hydrogen or a straight or branched chain C1–C4 alkyl. In other preferred compounds $R_4$ is a hydrogen.

The $R_5$ substituent is a hydrogen, a hydroxy group, a =O, a halogen, a substituted carbocyclic moiety, an unsubstituted carbocyclic moiety, a substituted heterocyclic moiety, or an unsubstituted heterocyclic moiety. The carbocycle moiety contains one or two rings having a total of 6 to 10 carbon atoms. Preferred carbocycle moieties include phenyl and naphthalenyl. Preferred halogens are Cl, F, and Br. $R_5$ may also be —$SiMe_3$.

The heterocyclic moiety has one or two heteroatoms and comprises either a single 3- to 6-membered ring or two rings with a total of 9 members. The permissible heteroatoms are N, S and O. In some preferred compounds $R_5$ is a hydrogen, a hydroxyl, or a six-membered heterocycle with a single heteroatom. A particularly preferred heteroatom is O. In other preferred compounds $R_5$ is either hydrogen or furfuryl.

Specific preferred heterocyclic moieties include, for example furanyl, furfuryl, imidazolyl, isobenzalolyl, pyridinyl, thiophenyl (thiofuranyl) and thiazolyl.

Both the carbocyclic and heterocyclic moieties (collectively "cyclic moieties") optionally are substituted at one or more positions. Preferably these moieties are substituted at 0–2 positions, depending on the size of the ring and other compatibilities recognized by those in the art, but halogen substituents preferably number 0–6. They specifically can be substituted at a single position.

The nature and positions of the possible substituents readily will be apparent to one of skill in the art. Examples of such substituents include a $CF_3$, methoxy, ethoxy, $N_2O$, halogen, OH, =O, and C1–3 alkyl. Preferred halogens are Cl, F and Br.

Illustrative of preferred compounds are 1-(5-hydroxyhexyl)-3,8-dimethylxanthine and 1-(5-hydroxyhexyl)-3-(2'-furfuryl)-methyl-8-methylxanthine.

The compounds of the present invention can be isolated as R- or S-enantiomers, or can be provided in the form of a racemic mixture. It is an increasingly common practice to market a drug with a chiral center as a racemate, regardless of whether it is only a single enantiomer that possesses the desired therapeutic activity. However, the approach of manufacturing and dosing drugs as racemic mixtures, therefore, means that each dose of a drug is contaminated with an equal weight of an isomer which may have no therapeutic value and has the potential to cause unsuspected side effects.

For example, the sedative thalidomide was marketed as a racemate. The desired sedative activity resided in the R-isomer, but the contaminating S-isomer is a teratogen, causing the birth defects in babies born to mothers using this drug. The R,R-enantiomer of the tuberculostatic ethambutol can cause blindness. The lethal side effects associated with the nonsteroidal anti-inflammatory drug benoxaprofen (Oraflex) might have been avoided had the drug been sold as a pure enantiomer. In view of these past problems, the compounds of the invention typically are synthesized as a single enantiomer. Several such synthetic schemes are set forth in Examples 1–4. Each enantiomer may be used independently or as a mixture, depending on such considerations as efficacy and toxic side effects.

In addition to their structural characteristics, the compounds of the present invention share an ability to inhibit the activity of cellular P-450 enzymes. Such inhibition readily may be determined by the skilled scientist using routine assays. An example of one such assay is provided in Example 5, below. Additional examples can be found in Kunze et al., Chem. Res. Toxicol. 6:649–56 (1993).

Pharmaceutical Formulations

The pharmaceutical compositions of the invention generally contain a therapeutically effective amount of one or more compounds of the invention, or their pharmaceutically acceptable salts. Pharmaceutically acceptable salts readily will be apparent to the skilled clinician. Preferably, these one or more compounds, or their pharmaceutically acceptable salts, are admixed with other pharmaceutically effective methylxanthine agents and a pharmaceutically acceptable excipient. The pharmaceutical formulations can contain isolated R- or S-enantiomers or racemic mixtures of these compounds.

A suitable formulation will depend on the nature of the disorder to be treated, the nature of the medicament chosen, and the judgment of the attending physician. In general, the inventive compounds are formulated either for oral administration or injection, although other modes of administration such as transmucosal or transdermal routes may be employed. Suitable formulations for these compounds, including pharmaceutically acceptable excipients, can be found, for example, in REMINGTON'S PHARMACEUTICAL SCIENCES, chapters 83–92, pages 1519–1714 (Mack Publishing Company 1990) (Remington's), which is hereby incorporated by reference.

The inventive compounds and their pharmaceutically acceptable salts can be employed in a wide variety of pharmaceutical forms. The preparation of a pharmaceutically acceptable salt largely will be determined by the chemical nature of the compound itself, and can be prepared by conventional techniques readily available.

Thus, if a solid carrier is used then the preparation can be tableted, placed in a hard gelatin capsule in powder or pellet form or in the form of a troche or lozenge. The amount of solid carrier will vary widely but preferably will be from about 25 mg to about 1 gram.

Where the composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions or suspensions may be considered, for example, aqueous gums, celluloses, silicates or oils and are incorporated in a soft gelatin capsule shell.

When a liquid carrier is used, the preparation may be in the form of a syrup, emulsion, soft gelatin capsule, sterile injectable liquid such as an ampule or nonaqueous liquid suspension.

A syrup formation will generally consist of a suspension or solution of the compound or salt thereof in a liquid carrier with a flavor or coloring agent. Examples of liquid carriers include ethanol, polyethylene glycol, coconut oil, glycerine and water.

Although other routes of administration are contemplated, the pharmaceutical compositions of the invention preferably are suitable for oral and parenteral administration. Parenteral administration can include intravenous ("i.v."), intramuscular ("i.m."), subcutaneous ("s.c."), intranasal, intrarectal, intravaginal intraperitoneal ("i.p.") ex vivo culture, or topical delivery. Preferred administration is accomplished orally.

Additionally, the inventive compounds may be administered by, for example, intranasal or oral inhalation. Appropriate dosage forms for inhalation include an aerosol or a metered dose inhaler, as prepared by conventional techniques. Typical compounds for inhalation are in the form of a solution, suspension or emulsion that may be administered as a dry powder or in the form of an aerosol using a conventional propellant.

Appropriate dosage forms for each specific route of administration may be prepared by conventional techniques. A typical dosage form for parenteral administration is a solution or suspension of at least one inventive compound, or its pharmaceutically acceptable salt. The parenteral dosage form typically contains a parenterally acceptable sterile aqueous or non-aqueous carrier. The parenteral dosage form optionally contains a parenterally acceptable oil. Examples of such oils include polyethylene glycol, polyvinylpyrrolidone, lecithin, arachis oil, and sesame oil. Parenteral acceptability is known to the skilled clinician.

Formulation as a standard unit dose also is contemplated. Thus, the pharmaceutical compositions of the invention can be formulated, for example, for oral use in dosage unit form as a pill, a tablet, a caplet, or a capsule. These dosage units may each contain a therapeutically effective amount of one or more compounds of the invention. These dosage units also may contain sub-therapeutically effective amounts, where multiple units may be combined to achieve a therapeutically effective amount.

The amount of inventive compound in a unit dose will depend on many factors considered by the skilled clinician. Generally, however, dosage units prepared for oral use will contain from about 5 mg to about 5000 mg of and inventive compound. Preferred oral formulations contain from about 100 mg to about 2500 mg of compound, whereas other preferred formulations contain from about 500 mg to about 1500 mg. Such formulations conveniently can be administered one to six, and preferably, two or three times daily.

A typical parenteral unit dose can be from about 1 g to about 5 g and may be administered (i.v., i.p., i.m., or s.c.) over a course of 24 hours. A typical topical formulation contains from about 1% to about 4% by weight. An ex vivo culture concentration can be maintained from about 10 $\mu$M to about 500 $\mu$M.

Finally, the inventive compounds may be formulated with an effective amount of a target pharmaceutical agent, as described below.

Methods of the Invention

The methods of the present invention generally comprise administering a therapeutically effective amount of an inventive compound to a patient in need of such treatment. These methods modulate the metabolism of a target pharmaceutical agent. Some methods inhibit cellular P-450, and some specifically inhibit the isozyme P-450IA2. Preferred methods provide an increased circulating half-life of the target pharmaceutical agent. The patient may be a human or a non-human animal.

Some preferred methods further comprise coadministration of the inventive compound and a target pharmaceutical agent. It will be recognized that the optimal timing for administering the inventive compound will be determined by the clinician. Thus, in this context, coadministration means concurrent administration, not necessarily simultaneous administration. Preferably, however, the inventive compounds will be administered prior to or simultaneously with the target pharmaceutical agent.

The need for treatment ultimately will be based on the evaluation by a skilled clinician in the relevant art. Generally, however, a patient will be in need of such treatment when undergoing a procedure involving administering a target pharmaceutical agent which is metabolized by cellular P-450. Such a need also is indicated when the pharmaceutical agent is a methylxanthine or derivative thereof. This need is most acutely indicated when the methylxanthine or its derivative is known or discovered to be metabolized by cellular P-450.

Metabolism by cellular P-450 readily can be determined by one of skill in the art. One such method is presented in Example 5.

Typically, the methods of the invention result in increased circulating levels of the target pharmaceutical agent, thereby imparting an increased circulating half-life. Preferably this target pharmaceutical agent is a methylxanthine compound. Methylxanthines are well known to those in the art and generally include any compound based on a xanthine core moiety with at least one methyl substituent. Typically methylated are the 1, 3 and 7 positions of the xanthine ring. Some preferred methylxanthine compounds are substituted at one or more of the 1, 3, or 7 positions of the xanthine ring with a C1–C8 hydroxyalkyl or a C1–C8 oxoalkyl.

Specific non-limiting examples of methylxanthines are given in Goodman and Gilman's, Furrer et al., U.S. Pat. No. 4,207,321 (1980), Underiner et al., U.S. Pat. No. 5,354,756 (1994), THE MERCK INDEX, 12th ed. on CD-ROM, v. 12:1 (Chapman & Hall 1996), and references disclosed therein. Preferred methylxanthines include members of the lisofylline family of compounds, such as those described in Bianco et al., WO 93/17684 (1993), which is hereby incorporated by reference in its entirety. The LSF family of compounds include resolved enantiomers of 1-(ω-1)-hydroxyalkyl)-3,7-dimethylxanthines, and specifically includes (R) or (S) 1-(5-hydroxyhexyl)-3,7-dimethylxanthine. Additional preferred target pharmaceutical agents include the compounds of the present invention. Thus, the methods of the invention specifically include using the inventive compounds to inhibit their own metabolism or the metabolism of other compounds of the invention.

Determining a therapeutically effective amount is well within the purview of the skilled clinician and largely will depend on the exact identity of the inventive compound, particular patient characteristics and the nature of the target pharmaceutical agent. General guidance can be found, for example, in the publications of the International Conference on Harmonisation. Such a determination specifically will depend on such factors as toxicity and efficacy profile of the inventive compound.

In an initial clinical trial, a patient in need of treatment or a normal volunteer typically is administered an inventive compound at a specified dose, usually low, at specified intervals for a period of time. In the absence of adverse effects, as determined by the clinician, this procedure may be repeated with successively higher doses of inventive compound. In this way potential toxic side-effects and parameters, such as bioavailability, may be determined using methods readily known in the art. Some typical pre-clinical and clinical parameters that are monitored are found in Remington's at chapters 27 and 28, pages 484–528.

With the results of the toxicology studies in mind, clinical trials for efficacy are undertaken. For example, a patient being treated with a target pharmaceutical agent will be administered an inventive compound. The pharmaceutical agent typically would be one known, suspected, or subsequently determined to be metabolized by cellular P-450. Via well-known methods, the circulating levels of the target pharmaceutical agent may be determined. Analysis of this circulating level as a function of experimental dose will allow the clinician easily to determine efficacious, non-toxic doses of the inventive compound as relevant to any target pharmaceutical agent.

Preferably, the inventive compounds are administered orally. A exemplary daily dosage regimen for oral administration would typically be from about 0.01 mg/kg to about 20 mg/kg per day.

Although the foregoing detailed description and the following examples set forth representative preferred embodiments of the invention, they are not intended as exclusive embodiments. In view of the material presented, one of ordinary skill in the art readily would appreciate further embodiments that fall within the scope of the invention.

EXAMPLE 1

Synthesis of (R)-1-(5-Hydroxyhexyl)-3,8-dimethylxanthine (CT2408R)

A. Preparation of 5,6-Diamino-1-methyluracil

Glacial acetic acid (4.5 ml 75 mmol) was added to a suspension of 6-amino-1-methyluracil (5.66 g, 50 mmol) in hot water (100 ml). Sodium nitrite (4.14 g) was added in portions and the reaction mixture was stirred for 1 hour. The resulting solid was collected by filtration, washed with water (75 ml) and resuspended in water (100 ml). After warming to 50° C., sodium dithionite (10 g) was added in portions maintaining the reaction temperature between 50° C. and 55° C. After stirring at 50° C. for an additional 1 hour, the mixture was cooled to room temperature and filtered. The solid was washed with water (2×25 ml), with acetone (2×25 ml) and then dried under vacuum. Yield=5.6 g.

B. Preparation of 3,8-Dimethylxanthine

A solution of 1-methyl-5,6-diaminouracil (2.5 g) in acetic anhydride (25 ml) was heated at reflux for 2 hours and then concentrated. The residue was dissolved in 10% sodium hydroxide solution (50 ml) and heated at reflux for 2 hours. After cooling to room temperature the solution was acidified to pH 4 with concentrated hydrochloric acid. The product was filtered, washed with water (15 ml), with acetone (15 ml) and then dried under vacuum. Yield 1.8 g.

C. Preparation of 7-Benzyl-3,8-dimethylxanthine

A solution of sodium hydroxide (400 mg) in water (5 ml) was added to a suspension of 3,8-dimethylxanthine (1.80 g) in methanol (10 ml) at 70° C. and stirred for 1 hour. Benzyl bromide (1.2 ml) was added and the mixture was stirred at 70–80° C. for 5 hours. After evaporation of the solvent under reduced pressure, the residue was suspended in saturated aqueous ammonium chloride solution (50 ml) and extracted with ethyl acetate (3×75 ml). The combined extracts were washed with saturated aqueous sodium chloride solution (30 ml), dried over magnesium sulfate and concentrate. The product was purified by recrystallization from ethanol. Yield=1.06 g.

D. Preparation of (R)-1-(5-Acetoxyhexyl)-7-benzyl-3,8-dimethylxanthine

7-Benzyl-3,8-dimethylxanthine (500 mg, 1.85 mmol) was added to a suspension of sodium hydride (50.5 mg) in anhydrous DMSO (20 ml) and stirred for 30 min. (R)-5-acetoxy-1-chlorohexane (357 mg) (prepared according to Kline et al. U.S. Pat. No. 5,629,423 (1997)) was added and the mixture was heated at 70–80° C. for 12 h. After cooling to room temperature, the reaction was quenched by the addition of water (50 ml) and extracted with ethyl acetate (3×75 ml). The combined extracts were washed with water (2×50 ml), with saturated aqueous sodium chloride solution (50 ml), dried over magnesium sulfate and concentrated. The product was purified by flash chromatography (silica gel) eluting with ethyl acetate. Yield=638 mg.

E. Preparation of (R)-7-Benzyl-1-(5-hydroxyhexyl)-3,8-dimethylxanthine

A solution of (R)-1(5-Acetoxyhexyl)-7-benzyl-3,8-dimethylxanthine (500 mg) in methanol (20 ml) was treated with 1 M hydrochloric acid in ether (2.5 ml) and stirred for 12 hours. After evaporation of volatiles under reduced pressure, the residue was dissolved in ethyl acetate (100 ml), washed with saturated sodium bicarbonate solution (30 ml), dried over anhydrous magnesium sulfate and concentrated. Yield=420 mg.

F. Preparation of (R)-1-(5-Hydroxyhexyl)-3,8-dimethylxanthine, CT2408R

A solution of (R)-7-benzyl-1-(5-hydroxyhexyl)-3,8-dimethylxanthine (250 mg) in a mixture of acetic acid (10 ml) and ethyl acetate (10 ml) was hydrogenated in presence of palladium on carbon (50 mg) for 12 hours. The mixture was filtered through celite (5 g) and concentrated. The residue was dissolved in ethyl acetate (100 ml), washed with saturated sodium bicarbonate solution (50 ml), dried over magnesium sulfate and concentrated. The product was purified by flash chromatography (silica gel) eluting with 10% methanol/ethyl acetate. Yield=180 mg.

EXAMPLE 2

Synthesis of (S)-1-(5-Hydroxyhexyl)-3,8-dimethylxanthine (CT2408S)

A. Preparation of (S)-1-(5-Acetoxyhexyl)-7-benzyl-3,8-dimethylxanthine

First, (S)-5-acetoxy-1-bromohexane was prepared in the following manner.

(S)-5-Acetoxy-1-bromohexane

A solution of (S)-5-acetoxy-1-hydroxyhexane (33.1 g:0.206 mol) and carbon tetrabromide (75.47 g:0.227 mol) in dichloromethane (500 ml) was placed in round bottomed flask fitted with a magnetic stirrer bar and triphenyl phosphine (59.68 g:0.227 mol) was added in portions at room temperature. The reaction mixture was stirred for 6 hrs. The dichloromethane was removed under reduced pressure. The crude product was triturated with hexane (5×200 ml). The combined hexane solution was concentrated under reduced pressure. The crude product was further purified by flask chromatography over silica gel using hexane/10% ethyl acetate as eluant. Yield=32.46 g (70%).

7-Benzyl-3,8-dimethylxanthine (500 mg, 1.85 mmol) was added to a suspension of sodium hydride (50.5 mg) in anhydrous DMSO (20 ml) and stirred for 30 minutes. (S)-5-acetoxy-1-bromohexane (446 mg, 2 mmol) was added and the mixture was heated at 70–80° C. for 12 hours. After cooling to room temperature, the reaction was quenched by the addition of water (50 ml) and extracted with ethyl acetate (3×75 ml). The combined extracts were washed with water (2×50 ml), with saturated aqueous sodium chloride solution (50 ml), dried over magnesium sulfate and concentrated. The product was purified by flash chromatography (silica gel) eluting with ethyl acetate. Yield=411 mg.

B. Preparation of (S)-7-Benzyl-1-(5-hydroxyhexyl)-3,8-dimethylxanthine

A solution of (S)-1-(5-acetoxyhexyl)-7-benzyl-3,8-dimethylxanthine (350 mg) in methanol (20 ml) was treated with 1 M hydrochloric acid in ether (2.5 ml) and stirred for 12 hours. After evaporation of volatiles under reduced pressure, the residue was dissolved in ethyl acetate (100 ml), washed with saturated aqueous sodium bicarbonate solution (30 ml), dried over magnesium sulfate and concentrated. Yield=270 mg.

C. Preparation of (S)-1-(5-Hydroxyhexyl)-3,8-dimethylxanthine, CT2408S

A solution of (S)-7-benzyl-1-(5-hydroxyhexyl)-3,8-dimethylxanthine (200 mg) in a mixture of acetic acid (10 ml) and ethyl acetate (10 ml) was hydrogenated in presence of palladium on carbon (40 mg) for 12 hours. The mixture was filtered through celite (5 g) and concentrated. The residue was dissolved in ethyl acetate (100 ml), washed with saturated aqueous sodium bicarbonate solution (50 ml), dried over magnesium sulfate and concentrated. The product was purified by flash chromatography (silica gel) eluting with 10% methanol/ethyl acetate. Yield=140 mg.

EXAMPLE 3

Synthesis of (R)-3-(2-Furylmethyl)-1-(5-hydroxyhexyl)-8-methylxanthine

A. Synthesis of furfurylurea

Furfurylamine (5.0 g, 51.5 mmol) was slowly added to a stirring 1 M solution of anhydrous hydrogen chloride in ether (61.8 ml, 61.8 mmol) cooled to 0° C. The resulting slurry was swirled for 5 minutes then evaporated under reduced pressure to give furfurylamine hydrochloride as a pale yellow solid. This salt was dissolved in water (30 ml) then heated to 85° C. Potassium cyanate (4.2 g, 51.5 mmol) was added and the reaction stirred at 85° C. for 3 hours. After cooling to ambient temperature the solution was diluted with ethanol (100 ml). After 2 hours the resulting solid salts were removed by filtration and the filtrate was evaporated under reduced pressure to give a crude solid. Recrystallization from ethyl acetate/toluene gave a furfurylurea (7.0 g, 97% yield) as a tan solid.

B. Synthesis of 6-amino-1-furfuryluracil

A solution of furfurylurea (7.0 g, 50.0 mmol), cyanoacetic acid (4.7 g, 55.0 mmol), and acetic anhydride (50 ml) was heated to 95° C. for 3 hours. After cooling to ambient temperature the solution was concentrated under reduced pressure to give a crude intermediate that was stirred with water (30 ml). After concentrating, the residue was dissolved in water (100 ml) and treated with a 50% aqueous sodium hydroxide solution (10 ml) to give a pH of 13. This solution was heated at 70° C. for 30 minutes, cooled and filtered. The wet solids were stirred in boiling ethanol for 15 minutes, cooled to ambient temperature and filtered. The filtrate was evaporated under reduced pressure to give 6-amino-1-furfuryluracil (5.5 g, 53% yield) as an orange solid.

C. Synthesis of 5,6-Diamino-1-furfuryluracil

6-Amino-1-furfuryluracil (3.0 g, 14.5-mmol) was dissolved with heating in 30% aqueous acetic acid (30 ml) and then a solution of sodium nitrite (1.7 g, 24.6 mmol) in water (5 ml) was added dropwise. The reaction was heated to 70° C. for 30 min and then cooled to 0° C. The solids were collected by filtration and rinsed with cold water (20 ml). The solids were dissolved into concentrated aqueous ammonium hydroxide solution (10 ml) and then a solution of sodium hydrosulfite (9.8 g, 47.8 mmol) in water (30 ml) was added in one portion. After heating at 80° C. for 1 hour, the slurry was cooled to ambient temperature. The solids were collected by filtration, rinsed with water (4×50 ml) and vacuum dried over phosphorus pentoxide to give 5,6-diamino-1-furfuryluracil (1.72 g, 53% yield) as a brown solid.

D. Synthesis of 3-(2-Furylmethyl)-8-methylxanthine

A solution of 5,6-diamino-1-furfuryluracil (1.7 g, 7.7 mmol), trimethyl orthoformate (1.5 ml, 11.5 mmol), and p-toluenesulfonic acid monohydrate (15 mg, 0.08 mmol) in N,N-dimethylformamide (20 ml) was heated to 120° C. for 3 hours. The solvent was removed by distillation under reduced pressure to give a residue that was dissolved in water (70 ml) and treated with saturated aqueous sodium bicarbonate solution (10 ml). The solution was heated briefly to boiling and allowed to cool to ambient temperature. The solid was collected by filtration and stirred in a solution of ethanol (30 ml) and water (5 ml). The cooled solution was filtered and the solids rinsed with ethanol (2×20 ml) to give 3-(2-furylmethyl)-8-methylxanthine (1.38 g, 73%) as a tan solid.

E. Synthesis of 3-(2-Furylmethyl)-7-pivaloyloxymethyl-8-methylxanthine

To a stirring solution of 3-(2-furylmethyl)-8-methylxanthine (1.35 g, 5.48 mmol) in dimethyl sulfoxide (20 ml) was added sodium hydride (132 mg, 5.48 mmol) in one portion. After 30 minutes, chloromethyl pivalate (0.83 ml, 5.76 mmol) was added neat. The reaction was allowed to stir at ambient temperature for 24 h. The reaction was quenched by slow addition of water (75 ml). After stirring for 3 hours, the solid was filtered and rinsed with water (4×50 ml) and ethanol (50 ml). The product was recrystallized from ethanol/ethyl acetate/hexane to give 3-(2-Furylmethyl)-7-pivaloyloxymethyl-8-methylxanthine (1.36 g, 69%) as an off-white solid.

F. Synthesis of CT2412R

First, (R)-5-acetoxy-1-iodohexane was prepared in the following manner. A solution of (R)-5-acetoxy-1-chlorohexane (4.80 g:26.89 mmol) was added to sodium iodide (5.39 g:36 mmol) in a round bottomed flask fitted with magnetic stirrer bar and a reflux condenser and refluxed for 12 hrs with stirring. Acetone was removed under reduced pressure, The crude product was partitioned between ethyl acetate (50 ml) and water layer (60 ml). The organic layer was washed with 10% sodium thiosulphate solution followed by water (20 l), dried over anhydrous Mg SO4 and concentrated under reduced pressure. Yield=7 g (96%)

To a stirring solution of 3-(2-Furylmethyl)-7-pivaloyloxymethyl-8-methylxanthine (0.65 g, 1.8 mmol) in dimethyl sulfoxide (20 ml) was added sodium hydride in one portion. After 30 minutes, (R)-5-acetoxy-1-iodohexane (0.58 g, 2.16 mmol, prepared as above) was added neat. The reaction was allowed to stir at ambient temperature for 20 hours, quenched with water (70 ml) and then extracted with ethyl acetate (3×35 ml). The extracts were washed with saturated aqueous sodium chloride solution (30 ml), dried over sodium sulfate and concentrated to give a crude yellow oil. The product was purified by flash chromatography on silica gel (ethyl acetate) to give (R)-1-(5-Acetoxyhexyl)-3-(2-furylmethyl)-7-pivaloyloxymethyl-8-methylxanthine (0.41 g) as a yellow oil. The product oil was dissolved in methanol (20 ml) and treated with a sodium methoxide solution (25 wt. % in MeOH, 0.94 ml, 4.1 mmol). The reaction was allowed to stir at ambient temperature for 48 hours. The solution was diluted with ethyl acetate (40 ml) and quenched with water (20 ml). The organic phase was collected and washed with saturated aqueous sodium chloride solution (20 ml), dried over sodium sulfate and concentrated to give a yellow solid. Column chromatography on silica gel eluting with 10% methanol-ethyl acetate gave (R)-3-(2furylmethyl)-1-(5-hydroxyhexyl)-8-methylxanthin CT2412R (21 mg) as an off-white solid.

EXAMPLE 4

Synthesis of (S)-3-(2-Furylmethyl)-1-(5-hydroxyhexyl)-8-methylxanthine (CT2412S)

To a stirring solution of 3-(2-Furylmethyl)-7-pivaloyloxymethyl-8-methylxanthine (0.65 g, 1.8 mmol) in dimethyl sulfoxide (20 ml) was added sodium hydride in one portion. After 30 minutes, (S)-5-acetoxy-1-bromohexane (0.48 g, 2.16 mmol) was added neat. After stirring at ambient temperature for 20 hours, the reaction was quenched by addition of water (70 ml) and then extracted with ethyl acetate (3×35 ml). The combined extracts were washed with saturated aqueous sodium chloride solution (30 ml), dried over sodium sulfate and concentrated to give a yellow oil. Flash chromatography on silica gel eluting with ethyl acetate gave (S)-1-(5-Acetoxyhexyl)-3-(2-furylmethyl)-7-pivaloyloxymethyl-8-methylxanthine (0.43 g) as a yellow oil. The product oil was dissolved in methanol (20 ml) and treated with a sodium methoxide solution (25 wt. % in MeOH, 0.98 ml, 4.3 mmol). After stirring at ambient temperature for 48 hours, the solution was diluted with ethyl acetate (40 ml) and quenched with water (20 ml). The organic phase was washed with saturated aqueous sodium chloride solution (20 ml), dried over sodium sulfate and concentrated to give a yellow solid. Column chromatography on silica gel eluting with 10% methane ethyl acetate gave (S)-3-(2-furylmethyl)1-(5-hydroxyhexyl)-8-methylxanthine CT2412S (80 mg) as a white solid.

EXAMPLE 5

Measuring Inhibition of P-450 Activity

This example illustrates the ability of representative compounds to inhibit P-450 metabolism. The model system directly measures inhibition of P-4501A2-mediated metabolism in the physiological environment of human liver microsomes. Measurement of drug metabolism in a microsome system is directly predictive of liver metabolism in vivo. Thus, microsome data can be used to estimate the in vivo circulating half-life of compounds that are primarily metabolized in the liver.

Microsomes were prepared by standard techniques from four human livers. An example of such techniques is found in Eriksson, *Biochimica et Biophysica Acta.*, 508:155–64 (1978). Three sets of enantiomers, CT2408 R&S, CT2410 R&S, and CT2412 R&S, were evaluated for inhibition of caffeine metabolism to paraxanthine by P-450.

Briefly, the inventive compounds were preincubated in microsomes with NADPH at concentrations of 100 $\mu$M for 0, 5, and 20 minutes. Samples containing only buffer, LSF, or furafylline were used as controls.

At the end of the preincubation period, the samples were diluted in a solution of NADPH and caffeine. The samples then were incubated for twenty minutes. Hydroxyethyl theophylline was added as an internal standard, and the samples were analyzed for paraxanthine via HPLC. Decreased paraxanthine formation is indicative of inhibition of P-450-mediated caffeine metabolism.

Incubation conditions and analysis of paraxanthine

To 200 $\mu$L microsomal suspension (HL-124; 20 mg/mL protein, P-450 specific activity 0.24 nmol/mg protein) and 100 $\mu$L 8.0 mM NADPH (Sigma, tetrasodium salt) in 100 mM phosphate buffer pH 7.4 preincubated for 2 minutes at 37° were added 100 $\mu$L of test compound solution (400 $\mu$M) in phosphate buffer (100 $\mu$M, pH 7.4). The solution then was incubated at 37° with agitation for 0, 5, and 20 minutes at which times 100 $\mu$L of the solution was transferred to another tube containing 200 $\mu$L 12.5 mM caffeine and 200 $\mu$L 5.0 mM NADPH which had been warmed at 37° for 2 minutes. The suspensions then were incubated for 20 minutes, 200 $\mu$L acetonitrile added, and the tubes placed on ice.

After all incubations were finished, 50 $\mu$L β-hydroxyethyl theophylline (50 $\mu$g/mL, HET) was added as an internal standard. Paraxanthine standards were prepared in 0.5 mL phosphate buffer containing 2.0 mg boiled microsomal protein ranging in concentration from 0.433 to 13.9 nmol/sample.

The suspensions then were extracted for 5 minutes with 7.0 mL methylene chloride (Fisher Optima grade), centrifuged at 3,000 g and the aqueous layer aspirated to waste. An aliquot of the organic (5.5 mL) was then transferred to another tube, evaporated to dryness under nitrogen at 30°, and reconstituted in 20% methanol/water.

Thirty microliters of reconstituted sample were then applied to an Hewlett Packard 1050 HPLC system equipped with a Rainin Microsorb™ 4.6×100 mm column with 3 $\mu$m C-18 packing. Mobile phase was maintained at 1.0 mL/min and changed from 2:13:85 to 2:20:78 acetonitrile:methanol:25 mM phosphate buffer, pH 5 over 10 minutes, the column was then washed by increasing the acetonitrile to 20% prior to re-equilibration for the next injection. Column eluent was monitored at 285 nm and paraxanthine, HET, and caffeine respectively eluted at 5.3, 6.6, and 9.8 minutes. Theophylline eluted at 5.7 minutes and did not interfere with paraxanthine quantitation. Standard curves were linear with $r^2>0.999$.

Data are shown in Table 1. CT2408 R&S (1-(5-Hydroxyhexyl)-3,8-dimethylxanthine) and CT2412 R&S (3-(2-furylmethyl)-1-(5-hydroxyhexyl)-8-methylxanthine) showed similar inhibition. Neither CT2410 (1-(5-

Hydroxyhexyl)-3,7,8-trimethylxanthine) nor LSF ((R)-1-(5-Hydroxyhexyl)-3,7-dimethylxanthine) had any inhibitory effect. As expected, the positive control, furafylline (1,8-dimethyl-3-(2'furfuryl)-methylxanthine), showed good inhibition.

TABLE 1

| Sample | Time of Preincubation | | |
|---|---|---|---|
| | 0 minutes | 5 minutes | 20 minutes |
| Buffer | 100 (.002) | 95.4 (8.41) | 82.0 (3.04) |
| LSF | 101 (1.66) | 91.0 (3.52) | 85.8 (4.49) |
| FRF | 36.8 (6.18) | 13.9 (3.93) | 10.1 (1.89) |
| CT2408R | 95.2 | 73.9 | 46.6 |
| CT2408S | 97.2 | 71 | 41.8 |
| CT2410R | 92.8 | 87.8 | 88.3 |
| CT2410S | 101 | 91.0 | 83.5 |
| CT2412R | 101 | 82.8 | 56.3 |
| CT2412S | 98.7 | 75.6 | 51.7 |

Units are in expressed in percent of P-450 activity remaining, as normalized to a control sample containing no inhibitor and incubated for 0 minutes. Standard deviations are shown in parenthesis.

What we claim is:

1. A compound that inhibits the activity of cellular P-450 and that has the formula:

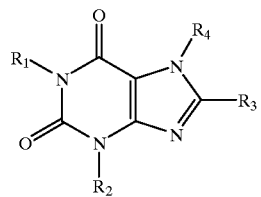

wherein $R_1$ is independently a resolved enantiomer or a racemic mixture of an ω-1 secondary alcohol-substituted C5–C8 alkyl, optionally containing one or two nonadjacent oxygen atoms in place of a carbon atom, $R_2$ is a C1–C20 alkyl, a C2–C20 alkenyl or C2–C20 alkynyl, which optionally contains one or two non-adjacent N or O atoms in place of a carbon atom and is substituted by furyl $R_3$ is methyl, optionally substituted by a C1–C7 alkyl, C2–C7 alkenyl, or C2–C7 alkynyl $R_4$ is hydrogen.

2. A method of treatment comprised of administering to a patient a therapeutically effective amount of an inhibitor of cellular P-450, wherein said inhibitor comprises a compound according to Formula I and administering a second, different compound which is a methylxanthine compound, wherein said methylxanthine compound is metabolized by P-450, and whereby said methylxanthine compound has a circulating half-life in the patient that is increased relative to treatment without said inhibitor,

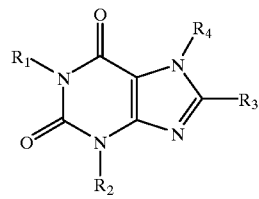

wherein Formula I has the following structure:
wherein $R_1$ is independently a resolved enantiomer or a racemic mixture of an ω-1 secondary alcohol-substituted C5–C8 alkyl, optionally containing one or two nonadjacent oxygen atoms in place of a carbon atom, $R_2$ is selected from the group consisting of a C1–C20 alkyl, a C2–C20 alkenyl and C2–C20 alkynyl which optionally contains one or two non-adjacent N or O atoms in place of a carbon atom and is optionally substituted by furyl $R_3$ is methyl, optionally substituted by a C1–C7 alkyl, C2–C7 alkenyl, or C2–C7 alkynyl $R_4$ is hydrogen or CH2—Y, wherein Y is a member of the group consisting of C1–C7 alkyl, C2–C7 alkenyl, and C2–C7 alkynyl.

3. The method of claim 2, wherein the compound of Formula I is 1-(5-hydroxyhexyl)-3-(2'-furfuryl)-8-methylxanthine or 1-(5-hydroxyhexyl)-3,8-dimethylxanthine.

4. The method of claim 2, wherein the compound of Formula I is the S-enantiomer.

5. The compound of claim 1, wherein the compound is 1-(5-hydroxyhexyl)-3-(2'-furfuryl)-8-methylxanthine.

6. A pharmaceutical composition comprising a pharmaceutically acceptable excipient and an amount of a compound of claim 1 effective to antagonize the activity of P-450.

7. The pharmaceutical composition of claim 6 that is suitable for oral delivery.

8. The method of claim 2, wherein the compound of Formula I is the R-enantiomer.

9. The pharmaceutical composition of claim 7, wherein the compound is formulated as a unit dose of from about 500 mg to about 1500 mg.

10. The compound of claim 5, wherein the compound is the R-enantiomer.

11. The compound of claim 5, wherein the compound is the S-enantiomer.

12. The method of claim 2 wherein said methylxanthine compound is substituted at one or more of the 1, 3, or 7 positions of the xanthine ring with a C1–C8 hydroxyalkyl or a C1–C8 oxoalkyl.

13. The method of claim 12, wherein said methylxanthine is 1-(5-hydroxyhexyl)-3,7-dimethylxanthine.

14. The method of claim 13, wherein said methylxanthine is the R-enantiomer.

* * * * *